United States Patent [19]

Mayer et al.

[11] 4,107,139
[45] Aug. 15, 1978

[54] 1-OXA-4,8-DIAZASPIRO[4,5]DECANES AND POLYMERS STABILIZED AGAINST UV LIGHT WITH THESE COMPOUNDS

[75] Inventors: Norbert Mayer, Gersthofen; Gerhard Pfahler, Augsburg; Hartmut Wiezer, Gersthofen, all of Fed. Rep. of Germany

[73] Assignee: Hoechst Aktiengesellschaft, Frankfurt am Main, Fed. Rep. of Germany

[21] Appl. No.: 823,145

[22] Filed: Aug. 9, 1977

[51] Int. Cl.$^2$ .................. C07D 498/10; C08K 5/35
[52] U.S. Cl. .................. 260/45.8 NZ; 260/45.8 NT; 260/293.63; 260/293.66
[58] Field of Search ............ 260/293.66, 293.63, 260/45.8 NZ

[56] References Cited

U.S. PATENT DOCUMENTS

| | | | |
|---|---|---|---|
| 3,431,233 | 3/1969 | Murayama et al. | 260/45.8 NZ |
| 3,534,048 | 10/1970 | Murayama et al. | 260/293.66 |
| 3,542,729 | 11/1970 | Murayama et al. | 260/45.8 NZ |
| 3,692,778 | 9/1972 | Murayama et al. | 260/293.66 |
| 3,720,670 | 3/1973 | Nakanishi et al. | 260/293.66 |
| 3,723,442 | 3/1973 | Nakanishi et al. | 260/293.66 |
| 3,856,797 | 12/1974 | Arimura et al. | 260/293.66 |
| 3,859,293 | 1/1975 | Murayama et al. | 260/45.8 NZ |
| 3,933,735 | 1/1976 | Murayama et al. | 260/45.8 NZ |
| 4,028,351 | 6/1977 | Taccone | 260/293.66 |

*Primary Examiner*—Donald E. Czaja
*Assistant Examiner*—R. A. White
*Attorney, Agent, or Firm*—Connolly and Hutz

[57] ABSTRACT

New 1-oxa-4,8-diazaspiro[4,5]decanes are prepared by reacting a dimethyl-dialkyl-piperidone with an α-hydroxyamide in the presence of a condensation catalyst. The compounds can be used as UV stabilizers for polymers.

9 Claims, No Drawings

1-OXA-4,8-DIAZASPIRO[4,5]DECANES AND POLYMERS STABILIZED AGAINST UV LIGHT WITH THESE COMPOUNDS

The invention relates to new 1-oxa-4,8-diazaspiro[4,5]decanes, which may be used to protect organic materials from the destructive action of ultraviolet light, as well as a process for their preparation.

The compounds correspond to the formula

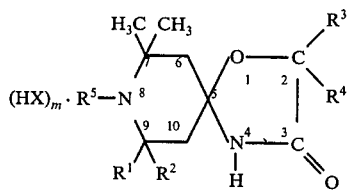

in which $R^1$ and $R^2$ are the same or different, straight-chained or branched alkyl radicals having 1 to 12 carbon atoms, or $R^1$ and $R^2$, together with the carbon atom to which they are bonded, form an optionally methyl-substituted cyclopentyl, cyclohexyl or 2,2,6,6-tetramethylpiperidyl ring, of which the carbon atom 4 is identical to the carbon atom 9 of the spiro system, $R^3$ and $R^4$ are the same or different and represent hydrogen atoms, alkyl radicals or isoalkyl radicals having 1 to 30 carbon atoms, or represent aryl radicals having 6 or 10 carbon atoms optionally substituted by a halogen atom or by an alkyl radical having 1 to 4 carbon atoms, or aralkyl radicals having 7 to 10 carbon atoms, or $R^3$ and $R^4$ together with the carbon atom to which they are bonded, form a cycloalkyl group having 4 to 20 carbon atoms, which may be substituted by $C_1$ to $C_4$ alkyl groups, or an optionally alkyl-substituted pyrrolidine or piperidine group, the ring nitrogen atom of which cannot be in the α-position to the spiro atom, $R^5$ represents a hydrogen atom, an oxygen atom, a hydroxyl group or an alkyl group having 1 to 4 carbon atoms, and HX represents a non-oxidizing mineral acid or an aliphatic or aromatic sulfonic or phosphonic acid, an aliphatic mono-, di- or polycarboxylic acid or an aromatic mono- or dicarboxylic acid and $m$ = O or 1 but when > N—$R^5$ does not have a basic reaction, is always O.

Examples of the 7,7-dimethyl-9,9-dialkyl-1-oxa-3-oxo-4,8-diazaspiro[4,5]decanes are, for example:

2,7,7,9,9-pentamethyl-1-oxa-3-oxo-4,8-diazaspiro[4,5]decane
2-ethyl-7,7,9,9-tetramethyl-1-oxa-3-oxo-4,8-diazaspiro[4,5]decane
2-propyl-7,7,9,9-tetramethyl-1-oxa-3-oxo-4,8-diazaspiro[4,5]decane
2-butyl-7,7,9,9-tetramethyl-1-oxa-3-oxo-4,8-diazaspiro[4,5]decane
2-isobutyl-7,7,9,9-tetramethyl-1-oxa-4,8-diazaspiro[4,5]decane
2-pentyl-7,7,9,9-tetramethyl-1-oxa-3-oxo-4,8-diazaspiro[4,5]decane
2-isopentyl-7,7,9,9-tetramethyl-1-oxa-3-oxo-4,8-diazaspiro[4,5]decane
2-isoheptyl-7,7,9,9-tetramethyl-1-oxa-3-oxo-4,8-diazaspiro[4,5]decane
2-phenyl-7,7,9,9-tetramethyl-1-oxa-3-oxo-4,8-diazaspiro[4,5]decane
2,2,7,7,9,9,-hexamethyl-1-oxa-3-oxo-4,8-diazaspiro[4,5]decane
2,2-diethyl-7,7,9,9-tetramethyl-1-oxa-3-oxo-4,8-diazaspiro[4,5]decane
2,2-dipropyl-7,7,9,9-tetramethyl-1-oxa-3-oxo-4,8-diazaspiro[4,5]decane
2,2-dibutyl-7,7,9,9-tetramethyl-1-oxa-3-oxo-4,8-diazaspiro[4,5]decane
2,2-dipentyl-7,7,9,9-tetramethyl-1-oxa-3-oxo-4,8-diazaspiro[4,5]decane
2-ethyl-2,7,7,9,9-pentamethyl-1-oxa-3-oxo-4,8-diazaspiro[4,5]decane
2-propyl-2,7,7,9,9-pentamethyl-1-oxa-3-oxo-4,8-diazaspiro[4,5]decane
2-isopropyl-2,7,7,9,9-pentamethyl-1-oxa-3-oxo-4,8-diazaspiro[4,5]decane
2-butyl-2,7,7,9,9-pentamethyl-1-oxa-3-oxo-4,8-diazaspiro[4,5]decane
2-isobutyl-2,7,7,9,9-pentamethyl-1-oxa-3-oxo-4,8-diazaspiro[4,5]decane
2-pentyl-2,7,7,9,9-pentamethyl-1-oxa-3-oxo-4,8-diazaspiro[4,5]decane
2-isopentyl-2,7,7,9,9-pentamethyl-1-oxa-3-oxo-4,8-diazaspiro[4,5]decane
2-hexyl-2,7,7,9,9-pentamethyl-1-oxa-3-oxo-4,8-diazaspiro[4,5]decane
2-heptyl-2,7,7,9,9-pentamethyl-1-oxa-3-oxo-4,8-diazaspiro[4,5]decane
2-nonyl-2,7,7,9,9-pentamethyl-1-oxa-3-oxo-4,8-diazaspiro[4,5]decane
2-undecyl-2,7,7,9,9,pentamethyl-1-oxa-3-oxo-4,8-diazaspiro[4,5]decane
2-ethyl-2-butyl-7,7,9,9-tetramethyl-1-oxa-3-oxo-4,8-diazaspiro[4,5]decane
2-ethyl-2-pentyl-7,7,9,9-tetramethyl-1-oxa-3-oxo-4,8-diazaspiro[4,5]decane
2-ethyl-2-isopentyl-7,7,9,9-tetramethyl-1-oxa-3-oxo-4,8-diazaspiro[4,5]decane
2,7,7,9,9-pentamethyl-1-oxa-3-oxo-4,8-diaza-8-oxylspiro[4,5]decane
2-hexyl-2,7,7,9,9-pentamethyl-1-oxa-3-oxo-4,8-diaza-8-oxylspiro[4,5]decane
2,2-diethyl-7,7,9,9-tetramethyl-1-oxa-3-oxo-4,8-diaza-8-oxylspiro-[4,5]decane
2,2,4,4,-tetramethyl-7-oxa-13-oxo-3,14-diazadispiro[5,1,4,2]tetradecane
2,2,4,4-tetramethyl-7-oxa-14-oxo-3,15-diazadispiro[5,1,5,2]pentadecane
2,2,4,4-tetramethyl-7-oxa-20-oxo-3,21-diazadispiro[5,1,11,2]heneicosane.

The different nomenclature of the last three compounds is derived from the IUPAC regulations (cf. Hellwinkel "Die systematische Nomenklatur der Organischen Chemie", Springer-Verlag, Heidelberg).

The spiro compounds of the invention in which $m$ = O and $R^5$ = H are obtainable by means of a condensation reaction between a 2,2-dimethyl-6,6-dialkylpiperidone, or a salt thereof, and a α-hydroxyamide in accordance with the following reaction equation:

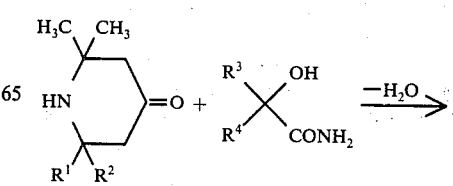

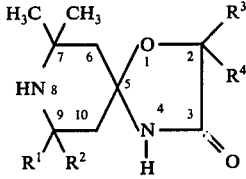

$R^1$, $R^2$, $R^3$ and $R^4$ having the meanings given above. The reaction is advantageously carried out in an organic solvent, preferably a lower aliphatic carboxylic acid and especially in glacial acetic acid, in the presence of a water-removing agent, such as, for example, polyphosphoric acid, or preferably sulfuric acid. The reaction temperature is 20° to 180°, preferably 40° to 120° and especially 50° to 80° C.

When using glacial acetic acid as solvent, equimolar amounts of piperidone and α-hydroxyamide are introduced into 3 to 10 times the amount by weight of glacial acetic acid and calculated on piperidone twice, or when the α-hydroxyamide contains a basic centre three times, the molar amount of concentrated sulfur acid is added dropwise, whereupon the mixture is heated. The reaction temperature selected may be between 40° and 120° C. In the course of the reaction the sulfuric acid salts of the compounds of the invention are generally precipitated, otherwise the mixture must be concentrated. The free bases are obtained from the salts so produced, by treating with ammonia or alkali hydroxide solution, and these bases may be converted, preferably in an organic solvent or water, into the salts of inorganic and organic acids. The compounds, in which $m = O$ and $R^5 = H$, may be alkylated with alkyl halides, preferably alkyl bromides or iodides. The methyl group may also be introduced by reacting with formic acid and aqueous formaldehyde solution, $CO_2$ being split off. By treating the compounds in which $R^5 = H$ with hydrogen peroxide, compounds in which $R^5 = O$ are produced.

The 2,2-dimethyl-6,6-dialkylpiperidones used as starting compounds can be produced according to methods known per se (for example, Beilstein, Volume 21, page 249; German Offenlegungsschrift No. 1,695,753); the α-hydroxyamides are obtained in accordance with the following reaction scheme:

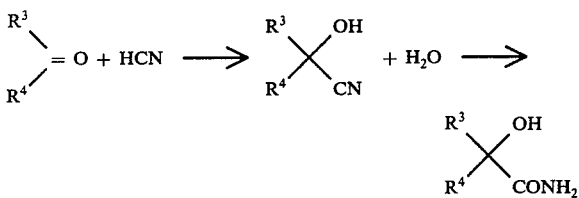

The two reaction steps can be carried out according to known processes. To hydrolyse the cyanohydrins, acids, preferably sulfuric acid, to which a quantity of water equimolar to the cyanohydrin has been added, or alkaline $H_2O_2$ (Houben-Weyl, Methoden der organischem Chemie, 4th Edition, Volume 3, pages 662–663) may be used. An especially suitable process is carried out by way of the imino ether hydrochlorides in accordance with the following reaction equation:

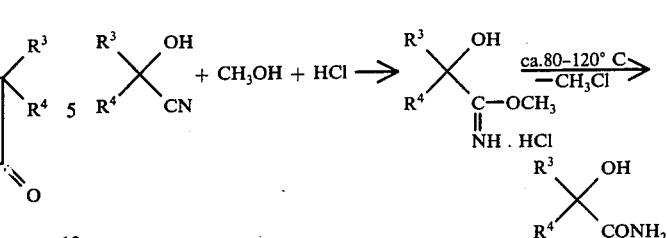

The imino ether hydrochloride does not, however, need to be purified before the pyrolysis.

There are limits imposed upon the synthesis of the new 1-oxa-4,8-diazaspiro[4,5]decanes since it is not as easy to produce the α-hydroxyamides from long-carbonyl compounds as it is from short-chained carbonyl compounds.

Suitable compounds for the production of the α-hydroxyamides to be used are, for example, those that can be obtained from the cyanohydrins of the following carbonyl compounds: formaldehyde, acetaldehyde, propionaldehyde, butyraldehyde, isobutyraldehyde, valeraldehyde, isovaleraldehyde, capronaldehyde, 2-ethylbutyraldehyde, oenanthaldehyde, 2-ethylcapronaldehyde, caprylaldehyde, pelargonaldehyde, isononylaldehyde, caprinaldehyde, isodecylaldehyde, laurinaldehyde, benzaldehyde, hydrocinnamaldehyde, also acetone, methyl ethyl ketone, methyl propyl ketone, methyl isopropyl ketone, hexan-2-one, methyl isobutyl ketone, heptan-2-one, heptan-3one, heptan-4-one, octan-2-one, octan-3-one, nonan-2-one, nonan-5-one, undecan-6-one, tridecan-2-one, methyl isopentyl ketone, ethyl isopentyl ketone, diethyl ketone, dibenzyl ketone, cyclopentanone, cyclohexanone, cyclododecanone, benzophenone, acetophenone, propiophenone.

In the new compounds of the formula

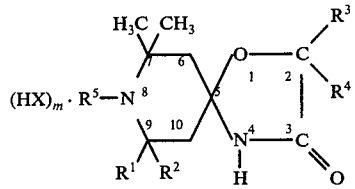

$R^1$ and $R^2$ represent straight-chained or - but not in α-position to the heterocycle - branched alkyl groups having 1 to 12, preferably 1 to 6, carbon atoms. $R^1$ and $R^2$ may be the same or different. The compounds in which $R^1$ and $R^2$ represent methyl, which may be derived from readily obtainable triacetone-amine, are especially important. Further, $R^1$ and $R^2$ together with the carbon atom 9 to which they are bonded, form an optionally methyl-substituted cyclopentane or cyclohexane ring, or represent a 2,2,6,6-tetramethylpiperidine group of which the carbon atom in the 4-position is the spiro atom.

Examples of $R^1$ are methyl and of $R^2$ methyl, isobutyl or hexyl, of $R^1$ and $R^2$ together with the carbon atom 9 bonding them, cyclopentyl, cyclohexyl and 2,2,6,6-tetramethylpiperidyl.

The radicals $R^3$ and $R^4$ stem from the α-hydroxyamides used, are the same or different and represent hydrogen, straight-chained or branched alkyl groups having 1 to 30 carbon atoms, an optionally halogen-substituted, preferably chlorine-substituted or alkylsubstituted (wherein th alkyl group may consist of 1 to 4 carbon atoms) aryl radical having 6 or 10 carbon atoms or an aralkyl radical having 7 to 10 carbon atoms, of which 1 to 4 carbon atoms belong to the aliphatic chain.

Depending on whether the α-hyroxyamide used was produced from an aldehyde or ketone, the following are preferred for $R^3$ and $R^4$.

If α-hydroxyamides synthesized from aldehydes are used, $R^3$ is hydrogen whereas $R^4$ may be hydrogen, or an alkyl group having 1 to 30, preferably 1 to 17 and especially 1 to 11 carbon atoms. Further, $R^4$ may be an aryl radical having 6 or 10 carbon atoms (phenyl or naphthyl) optionally substituted by a halogen atom — preferably chlorine — or by an alkyl radical having 1 to 4 carbon atoms, or an aralkyl radical having 7 to 10 carbon atoms, wherein 1 to 4 carbon atoms belong to the aliphatic chain.

When using a α-hydroxyamide obtained from a ketone, $R^3$ is an alkyl group having 1 to 30, preferably 1 to 10 and especially 1 to 6 carbon atoms or an aralkyl radical having 7 to 10 carbon atoms, wherein the aliphatic chain has 1 to 4 carbon atoms. $R^4$ is in this case an alkyl radical having 1 to 30, preferably 1 to 17 and especially 1 to 11 carbon atoms, or an aryl radical having 6 or 10 carbon atoms optionally substituted by a halogen atom — preferably chlorine — or by an alkyl radical having 1 to 4 carbon atoms, or an aralkyl radical having 7 to 10 carbon atoms, wherein the aliphatic chain consists of 1 to 4 carbon atoms.

Examples of radicals $R^3$ are hydrogen, methyl, ethyl, propyl, isopropyl, butyl, isobutyl, pentyl, hexyl, heptyl, octyl, nonyl, decyl, undecyl, heptadecyl, benzyl, phenylethyl, and of radicals $R_4$, methyl, ethyl, propyl, isopropyl, butyl, isobutyl, 2-ethylbutyl, pentyl, isopentyl, 2-ethylpentyl, isohexyl, heptyl, isoheptyl, octyl, isooctyl, nonyl, isononyl, decyl, undecyl, dodecyl, tridecyl, tetradecyl, pentadecyl, heptadecyl, 4-isopropylphenyl, 4-methylbenzyl, phenyl, phenylethyl, 2-chlorophenyl, 3-chlorophenyl, 4-chlorophenyl, 1-naphthyl, 2-naphthyl and benzyl.

$R^3$ and $R^4$ may, finally, together with the carbon atom to which they are bonded, form a cycloalkyl group having 4 to 20, preferably 5 to 12 and especially 5 to 7 carbon atoms. The cycloalkyl group here may be substituted by $C_1$ to $C_4$-alkyl radicals. $R^3$ and $R^4$ may together with the carbon atom to which they are bonded form an optionally alkyl-substituted pyrrolidine or piperidine ring. The ring nitrogen atom in this may not be in the α-position to the spiro atom. Examples of rings formed by the incorporation of the spiro atom are cyclopentyl, 3-methylcyclopentyl, cyclohexyl, 2-methylcyclohexyl, 3-methylcyclohexyl, 4-methylcyclohexyl, cycloheptyl, cyclooctyl, cyclononyl, cyclodecyl, cycloundecyl, cyclododecyl, cyclotridecyl, cyclopentadecyl and piperidyl.

The radical $R^5$ is preferably hydrogen. It may also be an oxygen atom, a hydroxyl group or an alkyl group having 1 to 4 carbon atoms.

HX represents an inorganic or organic acid. The following may be mentioned: non-oxidizing mineral acids, aliphatic sulfonic or phosphonic acids having 1 to 30, preferably 1 to 18 carbon atoms, optionally alkylated aromatic sulfonic or phosphonic acids having 6 to 25, preferably 6 to 18 carbon atoms, wherein 1 to 3 alkyl groups having 1 to 16 carbon atoms may be present, further, aliphatic, straight-chained or branched mono- or dicarboxylic acids having 2 to 34, preferably 2 to 18 carbon atoms, or optionally also aliphatic polycarboxylic acids having up to 4 carboxyl groups and a total of up to 16 carbon atoms, or also aromatic, optionally $C_1$- to $C_4$-alkyl- or isoalkyl-substituted mono- or dicarboxylic acids having 7 to 25, preferably 7 to 19 carbon atoms.

The following are mentioned in particular: phosphoric acid and phorphorous acid, sulfuric acid, phenylphosphonic acid, camphorsulfonic acid, dodecylsulfonic acid, p-toluenesulfonic acid, alkylpolyglycolethersulfonic acid, alkarylpolyglycolethersulfonic acid, acetic acid, propionic acid, octanoic acid, 2-ethylhexanoic acid, lauric acid, stearic acid, tallow fatty acid, montanic acid, succinic acid, adipic acid, azelaic acid, citric acid, tricarballyl acid, benzoic acid, tolyl acids, p-tert.-butylbenzoic acid, phthalic acid and terephthalic acid.

That the invention relates both to free bases and to the above-mentioned salts, or in the case of polybasic acids optionally also to acid salts of 1-oxa-4,8-diazaspiro[4,5]decanes, is indicated in the general formula by $m$ being 0 or 1. In compounds in which the group $>$ N-$R^5$ is not capable of salt formation, $m$ is 0.

The 1-oxa-4,8-diazaspiro[4,5]decanes according to the invention impart to organic polymer compositions an extraordinary stability towards decomposition by the action of heat, and especially by ultraviolet radiation. Apart from the fact that the compounds in which $R^5 =$ O have a typical natural color (yellow to orange-red), the color properties of the organic polymer compositions are not impaired. In this property they are superior to the sterically hindered piperidine compounds which are known as excellent UV stabilizers, such as, for example, triacetone-amine, some of which tend towards decomposition and/or discoloring when heated. The new compounds are particularly valuable for the light stabilization of polyolefins, such as, for example, polyisoprene, polybutadiene, polystyrene and especially polypropylene and polyethylene of low and high density, also ethylene/propylene copolymers, ethylene/butene copolymers, ethylene/vinyl acetate copolymers, styrene/butadiene copolymers and acrylonitrile/styrene/butadiene copolymers.

Other organic polymers are polyvinyl chloride, polyvinyl acetate and copolymers of the corresponding monomers with other olefinically unsaturated monomers. The term organic polymer also includes, for example, polyacetals, polyesters, polyamides, polyacrylates, polyurethanes and epoxy resins.

The quantity of new compounds to be added to the organic polymers can vary considerably, depending on the type, the properties and the special uses of polymer to be stabilized. For most uses, 0.01 to 5 parts by weight, preferably 0.05 to 3 parts by weight, especially 0.1 to 1.5 parts by weight, calculated on the amount of synthetic polymer, are employed. One compound or a mixture of several compounds can be used.

The compounds according to the invention are incorporated into the organic polymer compositions according to customary methods. Thus, the stabilizer can be mixed in the form of a powder with the polymer. Alternatively, a solution, suspension or emulsion of the stabilizer can be incorporated into the polymer directly or into a solution, suspension or emulsion of the same, the solvent being subsequently removed.

The stabilizers are effective on their own or in admixture with one or more customary stabilizers, such as, for example, antioxidants, based on phenol and sulfide, UV-absorbers and agents for protection against light, phosphite stabilizers, metal compounds, peroxide decomposing agents, epoxy stabilizers, polyhydric alcohols and also together with antistatic agents, flameproofing agents and pigments.

Examples of suitable antioxidants are those of the sterically hindered phenol type, such as 2,6-di-t.-butyl-p-cresol, 1,6-dioctadecyl-p-cresol, 4,4'-butylidene-bis(2,6-di-t.-butylphenol), 4,4'-thio-bis-(2-t.-butyl-b 5-methylphenol), phenolic triazine compounds, thiodipropionic acid esters of fatty alcohols, dioctadecyl sulfide and desulfide.

The UV absorbers and agents for protection against light include, for example 2-(2'-hydroxyphenyl)-benztriazoles, such as, 2-(2'-hydroxy-5'-methylphenyl)-benztriazole, 2-hydroxy-benzophenones such as 2-hydroxy-4-octoxybenzophenone, stabilizers from the group salicylates, such as octylphenyl salicylate, nickel chelates and oxalic acid diamides.

Trisnonylphenyl phosphite, trislauryl phosphite or also esters of pentaerythritol phosphite may be mentioned as phosphites.

By metal compounds known as stabilizers there are to be understood in this connection: calcium, barium, strontium, zinc, cadmium, magnesium, aluminum and lead soaps of aliphatic carboxylic acids or hydroxycarboxylic acids having approximately 12 to 32 carbon atoms, salts of the mentioned metals with aromatic carboxylic acids, such as benzoates or salizylates as well as (alkyl-)phenolates of these metals, also organotin compounds, such as, for example dialkyltin thioglycolates and carboxylates.

Known epoxy stabilizers are, for example, epoxidized higher fatty acids, such as epoxidized soya bean oil, tall oil, linseed oil or epoxidized butyloleate as well as epoxides of long-chained α-olefins.

Polyhydric alcohols may be, for example, pentaerythritol, trimethylol propane, sorbitol or mannitol, that is, preferably alcohols having 5 or 6 carbon atoms and 3 to 6 OH-groups.

An effective stabilizer combination for poly-α-olefins, such as for example, high, medium and low pressure polymers of $C_2$ to $C_4$-α-olefins, especially polyethylene and polypropylene, or of copolymers of such α-olefins consists, based on 100 parts by weight of polymer, for example of 0.01 to 5 parts by weight of one of the compounds to be used according to the invention, 0.05 to 5 parts by weight of a phenolic stabilizer, optionally 0.01 to 5 parts by weight of a sulfur-containing costabilizer, as well as, optionally, 0.01 to 3 parts by weight of a basic or neutral metal soap, such as, for example, calcium stearate or zinc stearate, as well as, optionally, 0.1 to 5 parts by weight of a phosphite and optionally 0.01 to 5 parts by weight of a known UV stabilizer from the group alkoxyhydroxybenzophenones, hydroxyphenylbenzotriazoles, benzylidenemalonic acid mononitrile esters or the so-called quenchers such as nickel chelates.

In the following the process for the production of the new compounds is illustrated by way of a few examples and the excellent efficiency of the same as agents for protecting plastics compositions against light is demonstrated.

EXAMPLE 1

2,7,7,9,9-Pentamethyl-1-oxa-3-oxo-4,8-diazaspiro[4,5]decane 31.0 g (0.2 mole) of triacetone-amine and 17.8 g (0.2 mole) of lactic acid amide are introduced into 200 g of glacial acetic acid. Then 43.1 g (0.44 mole) of concentrated $H_2SO_4$ are added dropwise while stirring, whereupon heating at 60° C is carried out for 40 hours. The precipitate formed on cooling is filtered off with suction (35 g ≙ 54% of the theoretical yield of the sulfuric acid salt of the desired compound), dissolved in approximately 50 ml of water and stirred into 100 ml of concentrated $NH_3$. The desired compound is precipitated in the course of this. It is filtered off with suction and recrystallized from acetone. Mp. 215° C.

EXAMPLES 2 to 7

The folowing were prepared analogously to Example 1 from equimolar amounts of triacetone-amine and α-hydroxyamide:

| Ex. No. | Compound | α-hydroxyamide used in which $R^3=$ | $R^4=$ | Product crystallized from | Mp ° C |
|---|---|---|---|---|---|
| 2 | 2-ethyl-2,7,7,9,9-pentamethyl-1-oxa-3-oxo-4,8-diazaspiro[4,5]decane | $CH_3$ | $C_2H_5$ | ethanol | 237 |
| 3 | 2-isopropyl-2,7,7,9,9-pentamethyl-1-oxa-3-oxo-4,8-diazaspiro[4,5]-decane | $CH_3$ | $i-C_3H_5$ | methanol | 241–242 |
| 4 | 2-isobutyl-2,7,7,9,9-pentamethyl-1-oxa-3-oxo-4,8-diazaspiro[4,5]-decane | $CH_3$ | $CH_2-CH(CH_3)_2$ | methanol | 218–219 |
| 5 | 2,2-diethyl-7,7,9,9-tetramethyl-1-oxa-2-oxo-4,8-diazaspiro[4,5]decane | $C_2H_5$ | $C_2H_5$ | ethanol | 254 |
| 6 | 2,2,4,4-tetramethyl-7-oxa-13-oxo-3,14-diazadispiro[5,1,4,2]tetradecane | $-(CH_2)_4-$ | | ethanol | 249 |
| 7 | 2,2,4,4-tetramethyl-7-oxa-14-oxo-3,15-diazadispiro[5,1,5,2]pentadecane | $-(CH_2)_5-$ | | ethanol | 276 |

EXAMPLE 8

2-Ethyl-7,7,9,9-tetramethyl-1-oxa-3-oxo-4,8-diazaspiro[4,5]decane 46.5 g (0.3 mole) of triacetone-amine and 30.9 g (0.3 mole) of 2-hydroxybutyramide are introduced into 300 g of glacial acetic acid. 62.7 g (0.64 mole) of concentrated $H_2SO_4$ are added dropwise while stirring. Stirring is then continued for 20 hours at 80° C. The glacial acetic acid is then distilled off in vacuo and the residue is stirred with ether/acetone. The precipitate produced is suction-filtered off, dissolved in 100 ml of water and stirred into 150 ml of concentrated $NH_3$. The precipitated compound is suction-filtered off and recrystallized from acetone. Mp. 196° C.

EXAMPLES 9 to 11

The following were prepared analogously to Example 8:

| Ex. No. | Compound | α-hydroxyamide used in which $R^3=$ | $R^4=$ | Product crystallized from | Mp. ° C |
|---|---|---|---|---|---|
| 9 | 2-phenyl-7,7,9,9-tetramethyl-1-oxa-3-oxo-4,8-diazaspiro- | H | $C_6H_5$ | ethanol | 222–223 |

-continued

| Ex. No. | Compound | α-hydroxyamide used in which R³= | R⁴= | Product crystallized from | Mp. °C |
|---|---|---|---|---|---|
| 10 | 2-isoheptyl-7,7,9,9-tetramethyl-1-oxa-3-oxo-4,8-diazaspiro[4,5]decane | H | i-C₇H₁₅ | ethyl acetate | 168 |
| 11 | 2,2-dipentyl-7,7,9,9-tetramethyl-1-oxa-3-oxo-4,8-diazaspiro[4,5]decane | C₅H₁₁ | C₅H₁₁ | ethyl acetate | 213–215 |

EXAMPLE 12

2-Propyl-7,7,9,9-tetramethyl-1-oxa-3-oxo-4,8-diazaspiro[4,5]decane 77.5 g (0.5 mole) of triacetone-amine and 58.3 g (0.5 mole) of 2-hydroxyvaleramide are introduced into 500 g of glacial acetic acid. 107.8 g (1.1 mole) of concentrated $H_2SO_4$ are then added dropwise while stirring and the whole is then stirred for 72 hours at 60° C. The glacial acetic acid is then distilled off under slightly reduced pressure, the oily residue is dissolved in water and stirred into concentrated $NH_3$. The substance precipitated is suction-filtered off and recrystallized from ethanol. Mp. 199° C.

EXAMPLE 13

2-Butyl-7,7,9,9-tetramethyl-1-oxa-3-oxo-4,8-diazaspiro[4,5]decane

The preparation of this compound is carried out analogously to Example 8 with 39.3 g (0.3 mole) of 2-hydroxycapronamide instead of 2-hydroxybutyramide for a period of 72 hours and at a temperature of 60° C. The product is recrystallized from methanol. Mp. 182° C.

EXAMPLES 14 to 17

The following compounds were produced in accordance with Example 13:

| Ex. No. | Compound | α-hydroxyamide used in which R³= | R⁴= | Product crystallized from | Mp °C |
|---|---|---|---|---|---|
| 14 | 2-isobutyl-7,7,9,9-tetramethyl-1-oxa-3-oxo-4,8-diazaspiro[4,5]decane | H | CH₃<br>\|<br>CH₂·CH<br>\|<br>CH₃ | ethyl acetate | 206–107 |
| 15 | 2-pentyl-2,7,7,9,9-pentamethyl-1-oxa-3-oxo-4,8-diazaspiro[4,5]decane | CH₃ | C₅H₁₁ | methanol | 186–188 |
| 16 | 2-nonyl-2,7,7,9,9-pentamethyl-1-oxa-2-oxo-4,8-diazaspiro[4,5]decane | CH₃ | C₉H₁₉ | acetone/water | 164–166 |
| 17 | 2-ethyl-2-isopentyl-7,7,9,9-tetramethyl-1-oxa-2-oxo-4,8-diazaspiro[4,5]decane | C₂H₅ | i-C₅H₁₁ | acetone | 208 |

EXAMPLE 18

2-Isopentyl-7,7,9,9-tetramethyl-1-oxa-3-oxo4,8-diazaspiro[4,5]decane

The preparation is carried out analogously to Example 13. When the reaction is complete approximately 100 ml of ether are added. The sulfuric acid salt of the desired compound then crystallizes out and after suction filtration is worked up analogously to Example 1. Mp. (ethyl acetate) 223°–224° C.

EXAMPLES 19 and 20

The following were produced in accordance with Example 18:

| Ex. No. | Compound | α-hydroxyamide used in which R³= | R⁴= | Product crystallized from | Mp °C |
|---|---|---|---|---|---|
| 19 | 2-butyl-2,7,7,9,9-pentamethyl-1-oxa-3-oxo-4,8-diazaspiro[4,5]decane | CH₃ | C₄H₉ | acetone/water | 199–200 |
| 20 | 2-isopentyl-2,7,7,9,9-pentamethyl-1-oxa-3-oxo-4,8-diazaspiro[4,5]decane | CH₃ | CH₃<br>\|<br>(CH₂)₂CH<br>\|<br>CH₃ | ethyl acetate | 199 |

EXAMPLE 21

2,2,7,7,9,9-Hexamethyl-1-oxa-3-oxo-4,8-diazaspiro[4,5]-decane

The preparation of this compound is carried out analogously to Example 13, using 77.5 g (0.5 mole) of triacetone-amine and 0.5 mole of 2-hydroxyisobutyramide. The sulfuric acid salt of the desired compound is precipitated during the reaction and is suctionfiltered off. Yield: 118 g ≙ 70% of the theoretical yield. Mp. (methanol) 238° C.

EXAMPLES 22 to 30

The procedure is as in Example 21 and the following products are obtained:

| Ex. No. | Compound | α-hydroxyamide used in which R³= | R⁴= | Product crystallized from | Mp °C |
|---|---|---|---|---|---|
| 22 | 2-pentyl-7,7,9,9-tetramethyl-1-oxa-3-oxo-4,8-diazaspiro[4,5]decane. | H | C₅H₁₁ | ethanol | 215 |
| 23 | 2-propyl-2,7,7,9,9-pentamethyl-1-oxa-3-oxo-4,8-diazaspiro[4,5]decane. | CH₃ | C₃H₇ | ethanol | 212 |
| 24 | 2-hexyl-2,7,7,9,9-pentamethyl-1-oxa-3-oxo-4,8-diazaspiro[4,5]-decane. | CH₃ | C₆H₁₃ | ethanol | 191–192 |
| 25 | 2-heptyl-2,7,7,9,9-pentamethyl-1-oxa-2-oxo-4,8-diazaspiro[4,5]-decane. | CH₃ | C₇H₁₅ | ethyl acetate | 187–188 |
| 26 | 2-undecyl-2,7,7,9,9-pentamethyl-1-oxa-2-oxo-4,8-diazaspiro[4,5]-decane. | CH₃ | C₁₁H₂₃ | ethyl acetate | 166 |
| 27 | 2-ethyl-2-butyl-7,7,9,9-tetramethyl-1-oxa-2-oxo-4,8-diazaspiro[4,5]decane. | C₂H₅ | C₄H₉ | ethyl acetate | 213 |
| 28 | 2-ethyl-2-pentyl-7,7,9,9-tetramethyl-1-oxa-2-oxo-4,8-diazaspiro[4,5]decane. | C₂H₅ | C₅H₁₁ | ethyl acetate | 198–199 |
| 29 | 2,2-dipropyl-7,7,9,9-tetramethyl-1-oxa-2-oxo-4,8-diazaspiro[4,5]- | C₃H₇ | C₃H₇ | ethanol | 242–243 |

| Ex. No. | Compound | α-hydroxya- mide used in which R³= | R⁴= | Product crystal- lized from | Mp ° C |
|---|---|---|---|---|---|
| | decane. | | | | |
| 30 | 2,2-dibutyl-7,7, 9,9-tetramethyl- 1-oxa-3-oxo-4,8- diazaspiro[4,5]- decane. | $C_4H_9$ | $C_4H_9$ | ethyl acetate | 225 |

EXAMPLE 31

2,2,4,4-Tetramethyl-7-oxa-20-oxo-3,21-diazas-piro[5,1,11,2]heneicosane 45.5 g (0.3 mole) of triacetone-amine and 68.1 g (0.3 mole) of 1-hydroxycyclododecane carboxamide are introduced into 300 g of glacial acetic acid. 62.7 g (0.64 mole) of concentrated $H_2SO_4$ are added while stirring.

Stirring is continued for 15 hours at 70° C and after cooling the reaction mixture, the sulfuric acid salt of the desired compound is suction-filtered off. Yield: 81 g = 59% of the theoretical yield. The salt is dissolved in ethanol/water with heating, the solution is stirred into concentrated aqueous ammonia, the precipitated amine base is suction-filtered off and recrystallized from cyclohexanone. The crystals are washed with ether. Mp. 273° C.

EXAMPLE 32

2,7,7,9,9-Pentamethyl-1-oxa-3-oxo-4,8-diaza-8-oxyl-spiro[4,5]decane 5 g of the compound according to Example 1, 50 ml of methanol, 9 ml of 30% $H_2O_2$, 0.2 g of $Na_2SO_4$ and 0.2 g of ethylenediamine tetraacetic acid are heated for 48 hours at 60° C. Concentration in vacuo is carried out, not to dryness, 20 ml of water is added, suction-filtering is effected followed by recrystallization from acetone/heptone. 3.5 g of orange-colored crystals are obtained. Mp. 170°–172° C.

EXAMPLES 33 and 34

The following were produced analogously to Example 32:

| Ex. No. | Compound | Starting product according to Example | Product crystal- lized from | Mp ° C |
|---|---|---|---|---|
| 33 | 2-hexyl-2,7,7,9, 9-pentamethyl-1- oxa-3-oxo-4,8-dia- za-8-oxylspiro- [4,5]decane | 24 | ether | 112–113 |
| 34 | 2,2-diethyl-7,7, 9-tetramethyl-1- oxa-3-oxo-4,8-di- aza-8-oxylspiro- [4,5]decane | 5 | heptane/ acetone | 128–130 |

EXAMPLE 35

2,2,7,7,8,9,9-heptamethyl-1-oxa-3-oxo-4,8-diazas-piro[4,5]decane 24.0 g of the compound according to Example 21 are introduced into 256 g of 90% formic acid. 162 g of 37% formaldehyde solution are added dropwise over a period of one hour, while stirring, at 20° to 30° C. The mixture is heated slowly to reflux and boiled until $CO_2$ evolution is complete (approximately 15 hours). The formic acid is then distilled off and, after cooling, the residue is stirred into concentrated aqueous ammonia. 15 g of white crystals having a melting point of 205° to 207° C are precipitated.

EXAMPLE 36

2-Isobutyl-2,7,7,8,9,9-hexamethyl-1-oxa-3-oxos-piro[4,5]decane

This compound was obtained as in the above Example from 28.2 g of the product of Example 4. Mp. 138° C.

EXAMPLE 37

2-Hexyl-2,7,7,9,9-pentamethyl-1-oxa-3-oxo-4,8-diazas-piro[4,5]decane p-tert.-butylbenzoate 3.10 g (0.01 mole) of the compound according to Example 24 and 1.78 g (0.01 mole) of p-tert.-butylbenzoic acid are heated for 15 minutes in 20 ml of methanol. After cooling, the precipitated white crystals are suction-filtered off. 3.7 g; Mp. 209°–211° C.

EXAMPLE 38

2-Hexyl-2,7,7,9,9-pentamethyl-1-oxa-3-oxo-4,8-diazas-piro[4,5]decane stearate

Preparation analogous to Example 37, with 2.84 g (0.01 mole) of stearic acid. 5.0 g of white crystals are obtained. Mp. 130 to 131° C.

EXAMPLE 39

2-Hexyl-2,7,7,9,9-pentamethyl-1-oxa-3-oxo-4,8-diazas-piro[4,5]decane succinate

Procedure as in Example 37, with 6.20 g (0.02 mole) of the compound of Example 24 and 1.18 g (0.01 mole) of succinic acid. 6.8 grams of white crystals having a melting point of 213°–214° C.

EXAMPLE 40

This Example shows the light-stabilizing action of the compounds according to the invention when using in a poly-α-olefin.

100 parts by weight of polypropylene having a melt index $i_5$ of approximately 6g/10 min (determined according to ASTM D1238-62 T) and a density of 0.96 were mixed with 0.10 parts by weight of pentaerythrityltetrakis [3-(3,5-ditert.-butyl-4-hydroxyphenyl)-propionate]

0.20 parts by weight of calcium stearate and 0.30 parts by weight of one of the compounds according to the invention, and the mixture was homogenized for 5 minutes at 200° C on a tworoller device. The plastics melt was then compressed 200° C into a plate 1 mm thick. Test bodies were stamped out of the cooled plate in accordance with DIN 53 455. The test bodies required as comparison samples were produced analogously but with the omission of the stabilizer to be tested.

To determine the light stability the samples were subjected to radiation with alternating light in a Xenotest-150-apparatus of the firm Original Hanau Quarzlampen GmbH. The radiation intensity was modulated by 6 IR windows and 1 UV window (DIN 53 387). The exposure time was measured in hours (= service life), after which the absolute elongation at break had reduced to 10%. The elongation at break was determined on a tensile testing machine of the firm Instron at a draw-off speed of 5 cm/min.

The results are compiled in the following table:

| Stabilizer of the invention according to Example | Service life (hours) |
| --- | --- |
| 4 | >1 000 |
| 7 | >1 000 |
| 9 | >1 000 |
| 11 | >1 000 |
| 21 | >1 000 |
| 26 | >1 000 |
| without(comparison) | 550 |

What is claimed is:

1. Compounds of the general formula

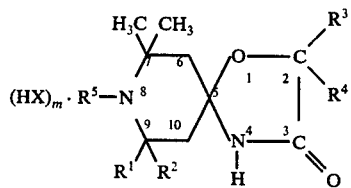

in which

R$^1$ and R$^2$ are the same or different, straight-chained or branched alkyl radicals having 1 to 12 carbon atoms, or R$^1$ and R$^2$, together with the carbon atom to which they are bonded, form an optionally methyl-substituted cyclopentyl, cyclohexyl or 2,2,6,6-tetramethylpiperidyl ring, of which the carbon atom 4 is identical to the carbon atom 9 of the spiro system, R$^3$ and R$^4$ are the same or different and represent hydrogen atoms, alkyl radicals or isoalkyl radicals having 1 to 30 carbon atoms, or represent aryl radicals having 6 or 10 carbon atoms optionally substituted by a halogen atom or by an alkyl radical having 1 to 4 carbon atoms, or aralkyl radicals having 7 to 10 carbon atoms, or R$^3$ and R$^4$ together with the carbon atom to which they are bonded, form a cycloalkyl group having 4 to 20 carbon atoms, which may be substituted by C$_1$ to C$_4$ alkyl groups, or an optionally alkyl-substituted pyrrolidine or piperidine group the ring nitrogen atom of which cannot be in the α-position to the spiro atom, R$^5$ represents a hydrogen atom, an oxygen atom, a hydroxyl group or an alkyl group having 1 to 4 carbon atoms, and HX represents a non-oxidizing mineral acid, an aliphatic or aromatic sulfonic or phosphonic acid, an aliphatic mono-, di- or polycarboxylic acid or an aromatic mono- or dicarboxylic acid and $m = 0$ or 1 but when > N—R$^5$ does not have a basic reaction, is always 0.

2. Compounds according to claim 1 in which R$^1$ and R$^2$ are methyl groups, R$^5$ = H and $m = 0$.

3. Compounds according to claim 2, in which R$^3$ is hydrogen and R$^4$ is methyl, ethyl, propyl, butyl, isobutyl, pentyl, 2-ethylpropyl, 2-ethylpentyl or phenyl.

4. Compounds according to claim 2 in which R$^3$ is a methyl group and R$^4$ is methyl, ethyl, propyl, isopropyl, butyl, isobutyl, pentyl, isopentyl, hexyl, heptyl, nonyl or undecyl.

5. Compounds according to claim 2, in which R$^3$ is ethyl and R$^4$ is butyl, pentyl or isopentyl.

6. Compounds according to claim 2, in which R$^3$ and R$^4$ are the same and represent methyl, ethyl, propyl, butyl or pentyl.

7. Compounds according to claim 2, in which R$^3$ and R$^4$ together with the carbon atom to which they are bonded represent a cyclopentyl, cyclohexyl or cyclododecyl ring.

8. Process for stabilizing halogen-free, aliphatic α-olefin homo and copolymers and chlorine-containing vinylhomo and copolymers against the damaging influence of light, wherein 0.1 to 5 parts by weight, based on the polymer, of a compound of claim 1 is added to the polymers.

9. Organic polymers stabilized against UV decomposition, containing 0.01 to 5% by weight, calculated on the polymers, of a stabilizer of claim 1.

* * * * *